United States Patent
Wong (10) Patent No.: US 9,339,611 B2
(45) Date of Patent: May 17, 2016

(54) RETRACTING SHEATH DETACHABLE SAFETY NEEDLE WITH MOVING SPRING

(71) Applicant: Becton, Dickinson and Company, Franklin Lakes, NJ (US)

(72) Inventor: Andrew Wong, East Hanover, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 483 days.

(21) Appl. No.: 13/793,655

(22) Filed: Mar. 11, 2013

(65) Prior Publication Data

US 2013/0261564 A1     Oct. 3, 2013

Related U.S. Application Data

(60) Provisional application No. 61/610,623, filed on Mar. 14, 2012.

(51) Int. Cl.
*A61M 5/00*     (2006.01)
*A61M 5/32*     (2006.01)

(52) U.S. Cl.
CPC .............. *A61M 5/3213* (2013.01); *A61M 5/326* (2013.01); *A61M 5/3273* (2013.01); *A61M 2005/3247* (2013.01)

(58) Field of Classification Search
CPC ............ A61M 5/3213; A61M 5/3243; A61M 5/3234; A61M 5/326; A61M 5/3273; A61M 2005/3267; A61M 2005/3247
USPC ........................................................ 604/198
See application file for complete search history.

(56) References Cited

U.S. PATENT DOCUMENTS

| 7,811,261 | B2 | 10/2010 | Rubinstein et al. |
| 8,591,474 | B2 | 11/2013 | Gratwohl et al. |
| 2005/0096599 | A1 | 5/2005 | Crawford et al. |
| 2011/0077592 | A1 | 3/2011 | Takemoto |
| 2013/0018312 | A1 | 1/2013 | Neale |

FOREIGN PATENT DOCUMENTS

| DE | 10-2006-042233 | 3/2008 | |
| FR | 2930161 | 10/2009 | |
| WO | WO 2006063015 A2 * | 6/2006 | ............ A61M 5/002 |

(Continued)

OTHER PUBLICATIONS

PCT International Preliminary Report on Patentability in PCT/US2013/031154, mailed Sep. 25, 2014, 8 pages.

(Continued)

*Primary Examiner* — Nathan R Price
*Assistant Examiner* — Morgan Lee
(74) *Attorney, Agent, or Firm* — Servilla Whitney LLC (57) ABSTRACT

A passive safety needle device is disclosed having a housing, a needle hub, a needle cannula, a retractable sheath, a spring to bias the retractable sheath in a distal direction to cover the distal end of the needle cannula, a radial protrusion to cause the spring to move from the proximal spring position to the distal spring position, and a catch to secure the distal end of the spring to the distal end of the housing. The spring may bias the retractable sheath in a distal direction to cover the distal end of the needle cannula. The radial protrusion causes the spring to move from a proximal spring position to the distal spring position towards the catch located at the distal end of the housing.

5 Claims, 8 Drawing Sheets (56) References Cited

FOREIGN PATENT DOCUMENTS

| WO | WO-2008/127195 | 10/2008 |
| WO | WO-2010/103920 | 9/2010 |
| WO | WO-2011/095480 | 8/2011 |

OTHER PUBLICATIONS

PCT International Search Report in PCT/US2013/031154, mailed Jul. 2, 2013, 4 pages.

* cited by examiner

RETRACTING SHEATH DETACHABLE SAFETY NEEDLE WITH MOVING SPRING

CROSS-REFERENCE TO RELATED APPLICATIONS

This application claims priority under 35 U.S.C. §119(e) to U.S. Provisional Application No. 61/610,623, filed Mar. 14, 2012, the disclosures of which are incorporated herein by reference in their entirety.

TECHNICAL FIELD

The subject invention relates generally to a safety needle device, and more particularly to a passive safety needle device having a housing, a needle hub, a needle cannula, a retractable sheath, a spring to bias the retractable sheath in a distal direction to cover the distal end of the needle cannula, a radial protrusion to cause the spring to move from the proximal spring position to the distal spring position, and a catch to secure the distal end of the spring to the distal end of the housing. The radial protrusion causes the spring to move from a proximal spring position and a distal spring position separated by a ledge towards the catch located at the distal end of the housing.

BACKGROUND

Needle devices are used throughout the medical industry for the injection and withdrawal of a wide variety of fluids and solutions into and from the human body. Because of the numerous potential hazards associated with the handling and manipulation of bodily fluids, and particularly blood, there are a number of known safety features that are frequently incorporated into various types of needle devices to protect the practitioner from accidental exposure to the needle.

Other prior safety needle devices having a retractable sheath require multi-component retraction and locking elements. Conventional retraction syringe assemblies often do not incorporate reuse prevention features, and thus, the retraction mechanism may be reset so the syringe barrel may be reused. The reuse of syringe assemblies without sterilization or sufficient sterilization is believed to facilitate the transfer of contagious diseases. Further, the retraction features of conventional syringes also often require the user to actively activate the retraction mechanism. Accordingly, the chance of human error in failure to activate or properly activate the retraction mechanism can lead to continued exposure of needles.

Prior retracting sheath safety needle devices have been developed to include a single-use cover assembly that obscures a substantial majority or an entirety of an injection needle from view before, during, and after an injection procedure. However, many injection procedures require that the practitioner know precisely the location and depth to which the needle is inserted in the patient's tissue to be sure that medication is delivered to an appropriate location.

There is a need in the art to provide a safety needle device having a passive activation mechanism that overcomes the deficiencies of the known retracting sheath safety needle devices and which allows for low part count, low part complexity, clear and unobstructed view of needle through sheath, relatively compact design and no rotation of the sheath during use.

SUMMARY

The present invention is directed to a safety needle device including a housing, a needle hub, a needle cannula, a retractable sheath, a spring to bias the retractable sheath in a distal direction to cover the distal end of the needle cannula, a radial protrusion to cause the spring to move from the proximal spring position to the distal spring position, and a catch to secure the distal end of the spring to the distal end of the housing. The housing includes a proximal end and a distal end having an opening. In one or more embodiments, the proximal end of the housing may be connectable to a luer connection or other fluid connector.

The retractable sheath may be disposed and movable in the opening and surrounds a needle cannula having a distal end and a proximal end. The needle cannula is mounted to a needle hub at the proximal end of the housing. The retractable sheath includes a radially enlarged proximal end defining a proximal spring position and a distal spring position separated by a ledge.

The spring may bias the retractable sheath in a distal direction to cover the distal end of the needle cannula. The spring includes a proximal end, a main body, and a distal end. In one embodiment, the radial protrusion may extend inwardly into housing to cause the spring to move from the proximal spring position to the distal spring position so that when the spring is extended, the distal end of the spring is secured to a catch at the distal end of the housing.

In one or more embodiments, the spring comprises a compression or coil spring having an enlarged coil portion on the distal end that has a diameter larger than the proximal end and main body of the spring. In one or more embodiments, the enlarged coil portion rests on the ledge when the spring is in the proximal spring position. In one or more embodiments, the enlarged coil portion rests on the catch to lock the retractable sheath when the spring is in the distal spring position.

In one or more embodiments, the catch is defined by inward ramps terminating in barbed ends.

In one or more embodiments, the retractable sheath fully covers the needle when the spring is in the distal spring position.

In one or more embodiments, the radial protrusion is configured to provide free movement between the radial protrusion and the proximal end and main body of the spring. In one or more embodiments, the radial protrusion is configured to provide hindered movement between the radial protrusion and the enlarged coil portion. In one or more embodiments, the radial protrusion compresses the enlarged coil portion to cause the enlarged coil portion to slip from the ledge and move from the proximal spring position to the distal spring position. In some embodiments, the radial protrusion is located on the proximal end of the housing. In other embodiments, the radial protrusion is located on the distal end of the housing.

The present invention is also directed to a safety needle device including a housing having a proximal end and a distal end having an opening; a needle cannula having a distal end and a proximal end mounted to a needle hub at the proximal end of the housing; a retractable sheath disposed an outer surface on the distal end of the housing surrounding the needle cannula, the retractable sheath having a larger diameter than the housing and having a radially enlarged proximal end defining a proximal spring position and a distal spring position separated by a ledge; a spring to bias the retractable sheath in a distal direction to cover the distal end of the needle cannula, the spring having a distal end; and a radially compressible member on the distal end of the spring having a larger diameter than the proximal end and main body of the spring; and a radially protrusion extending outwardly from housing to cause the radially compressible member to compress upon an application of force in the proximal direction to allow the spring to move from the proximal spring position to the distal spring position so that when the spring is extended, the distal end of the spring is secured to a catch at the distal end of the housing. In one or more embodiments, the proximal end of the housing may be connectable to a luer connection or other fluid connector.

In one or more embodiments, the radially compressible member rests on the ledge when the spring is in the proximal spring position. In one or more embodiments, the radially compressible member rests on the catch to lock the retractable sheath when the spring is in the distal spring position.

The present invention is also directed to a safety needle device including a housing having a proximal end and a distal end having an opening; a needle cannula having a distal end and a proximal end mounted to a needle hub at the proximal end of the housing; a needle hub having a radial protrusion extending outward into housing and a distal end having a ramped surface; a retractable sheath having a proximal end and distal end, the proximal end having a first flange forming a ledge with the ramped surface of the needle hub and a second flange to hold the retractable sheath in the housing, the retractable sheath surrounding a needle cannula having a distal end and a proximal end mounted to the needle hub at the proximal end of the housing, the first and second flange defining a proximal spring position and a distal spring position; a spring to bias the retractable sheath in a distal direction to cover the distal end of the needle cannula, the spring having a proximal end, a main body, and a distal end; the radially protrusion causing the spring to move from the proximal spring position to the distal spring position when the spring is extended; and a catch forming between the ramped surface and the second flange of the retractable sheath. In one or more embodiments, the proximal end of the housing may be connectable to a luer connection or other fluid connector.

In one or more embodiments, the spring comprises a reduced coil portion on the distal end having a smaller diameter than the proximal end and main body of the spring. In one or more embodiments, the reduced coil portion rests on the ledge when the spring is in the proximal spring position. In one or more embodiments, the reduced coil portion rests on the catch to lock the retractable sheath when the spring is in the distal spring position.

In one or more embodiments, the catch is defined by a recess formed between the outward ramped surface of the needle hub and the second flange of the retractable sheath.

In one or more embodiments, the radial protrusion is configured to provide free movement between the radial protrusion and the proximal end and main body of the spring. In one or more embodiments, the radial protrusion is configured to provide hindered movement between the radial protrusion and the reduced coil portion. In one or more embodiments, the radial protrusion enlarges the reduced coil portion to cause the reduced coil portion to slip from the ledge and move from the proximal spring position to the distal spring position. In one or more embodiments, the radial protrusion is located proximally to the ledge.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

In this disclosure, a convention is followed wherein the distal end of the device is the end closest to a patient and the proximal end of the device is the end away from the patient and closest to a practitioner.

FIGS. 1-10 illustrate an exemplary safety needle device 10 according to the present invention. Safety needle device 10 including a housing 20, a needle hub 30, a needle 40, a retractable sheath 50, a spring 60 to bias the retractable sheath 50 in a distal direction to cover the distal end of the needle 40, a radial protrusion 70 to cause the spring 60 to move from the proximal spring position 80 to the distal spring position 90, and a catch 100 to secure the distal end of the spring 60 to the distal end of the housing 20. In one or more embodiments, the housing 20 includes a proximal end 22 and a distal end 24 having an opening.

Figure 2:
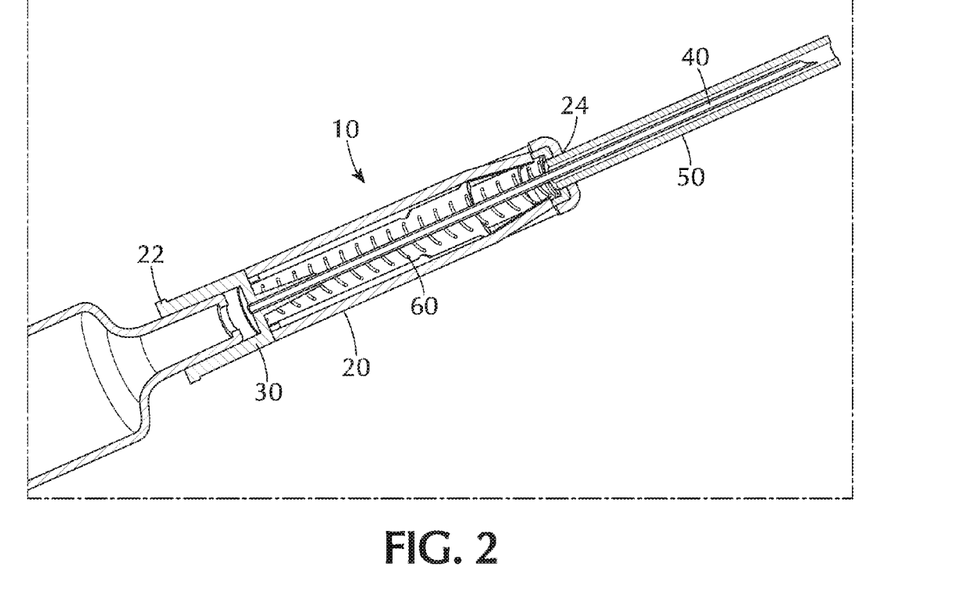
FIG. 2 is a plan view of the safety needle device.
Figure 3:
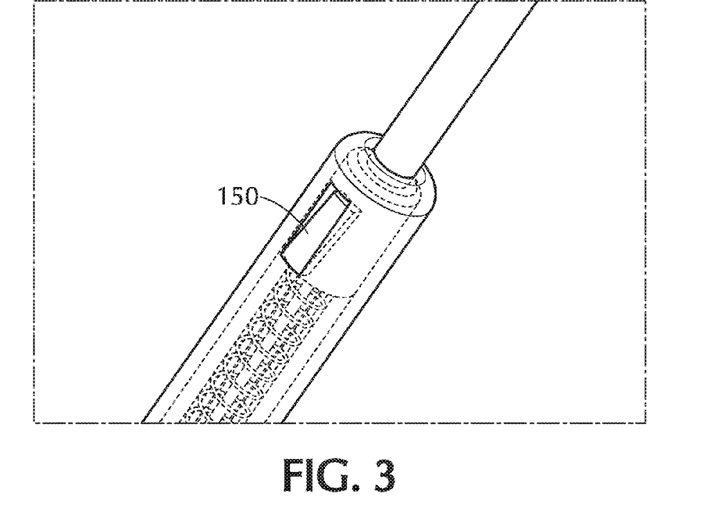
FIG. 3 is a plan view of the slots and rails of the safety needle device.

Generally speaking, safety needle device 10 is comprised of a needle 40, a housing 20, and a retractable sheath 50. Housing 20 includes a proximal end 22 and a distal end 24 having an opening. In one or more embodiments, the proximal end of the housing may be connectable to a luer connection or other fluid connector. Retractable sheath 50 is slidably mounted and movable in the opening to slidably accommodate and encase needle 40 projecting axially from housing 20. The term "retractable sheath" is intended to include any sort of tubular member and U-shaped member. The retractable sheath 50 is dimensioned to be compatible with the size and type of needle 40 as will be appreciated by those skilled in the art. The housing 20 may include a housing body portion with an internal hollow region (not shown) in which the retractable sheath 50 may move in the proximal direction. As shown in FIG. 2, needle 40 may be connected to a needle hub 30 disposed at the proximal end 22 of the housing 20 and having a blunted tip or beveled tip at the distal end. The needle 40 is disposed in the needle hub 30 in a manner as would be well understood in the art and which forms no part of the invention. The needle hub 30 may be integrally formed with the housing 20. The needle 40 extends from the needle hub 30 disposed in the housing 20 to a needle tip and is completely received within the retractable sheath 50 when the retractable sheath 50 is in a distal position. The needle tip is exposed from the retractable sheath 50 when the retractable sheath 50 is in a proximal position. FIG. 3 shows the internal slots and rails of the safety device.

Figure 1:
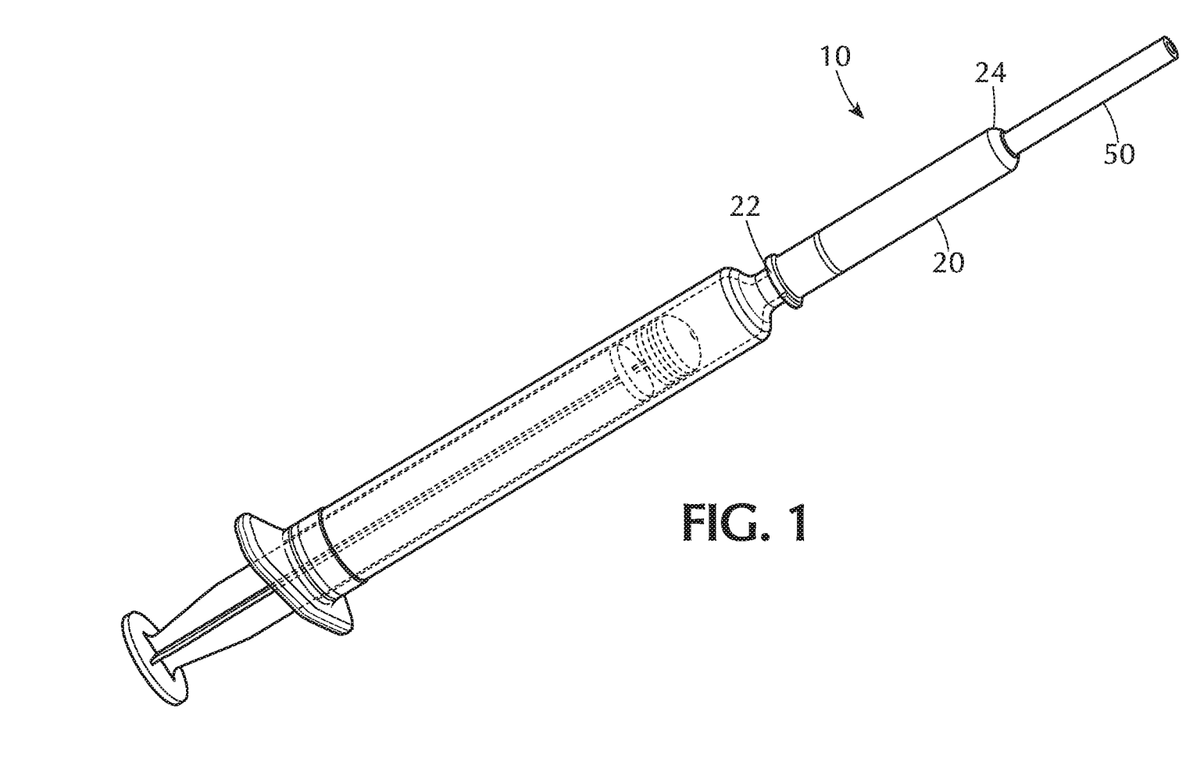
FIG. 1 is a perspective view of the safety needle device.

As illustrated in several of the drawings, most notably FIGS. 1 and 2, retractable sheath 50 is generally comprised of a tubular portion and is retractably slidable along the length of the needle 40 such that at least a substantial portion of needle 40 is exposed when the sheath 50 is in its retracted position (as illustrated in FIG. 2). The length of needle 40 extending outwardly from the needle hub 30 in a distal direction is partially or completely encased when retractable sheath 50 is in its non-retracted position (as illustrated in FIGS. 1 and 2).

The needle 40 in accordance with the present invention can be formed from conventional materials such as steel or more preferably stainless steel. It will be realized by the skilled artisan that medical grade plastics, composites, ceramics, or like materials can be substituted.

The inside diameter of the open-ended retracting sheath 50 is selected so that it will fit closely over needle 40. The retracting sheath 50 may be made of any suitable material, but preferably of a polymer which is tough enough to protect needle 40 and may be easily sterilized. The material is preferably transparent or translucent so that the position of needle 40 within retracting sheath 50 can be visually verified. Sheath 50 is preferably made of a transparent material, so that a health care worker can see the progress of needle 40 as it is emerging from sheath 50 to make sure that it is positioned where desired for an injection.

The retractable sheath 50 may be disposed and movable in the opening and surrounds a needle 40 having a distal end and a proximal end. The needle 40 is mounted to a needle hub 30 at the proximal end of the housing. The retractable sheath 50 includes a radially enlarged proximal end defining a proximal spring position 80 and a distal spring position 90 separated by a ledge 150. The retractable sheath 50 is spring loaded, and is supplied with the sheath completely or partially covering the needle 40.

The spring 60 may bias the retractable sheath 50 in a distal direction to cover the distal end of the needle 40. The spring 60 includes a proximal end, a main body, and a distal end. In one embodiment, the radial protrusion 70 may extend inwardly into housing 20 to cause the spring 60 to move from the proximal spring position 80 to the distal spring position 90 so that when the spring 60 is extended, the distal end of the spring 60 is secured to a catch 100 at the distal end of the housing. In this position, the spring impedes proximal movement of the retracting sheath, thereby protecting the needle tip.

Figure 4:
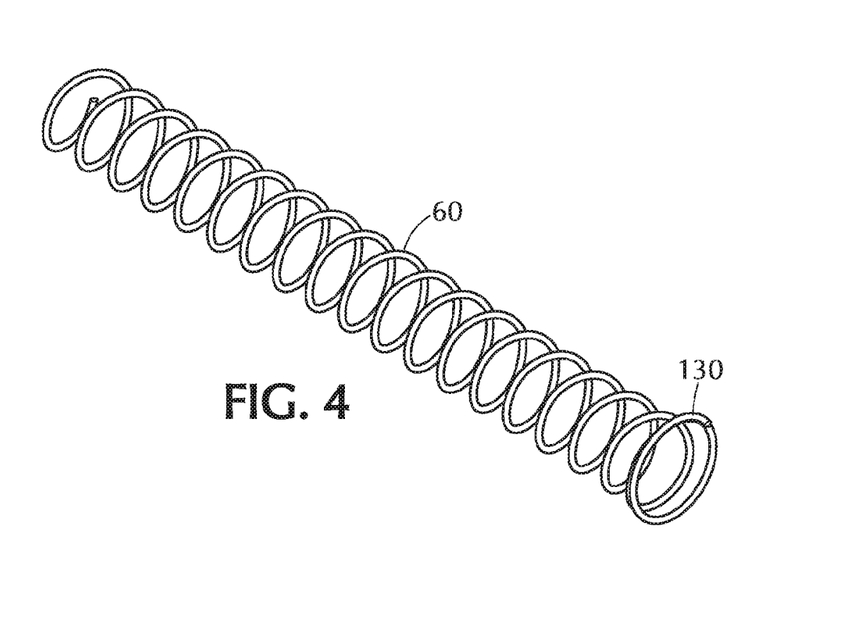
FIG. 4 is a perspective view of the spring of the safety needle device having an enlarged end coil.
Figure 5:
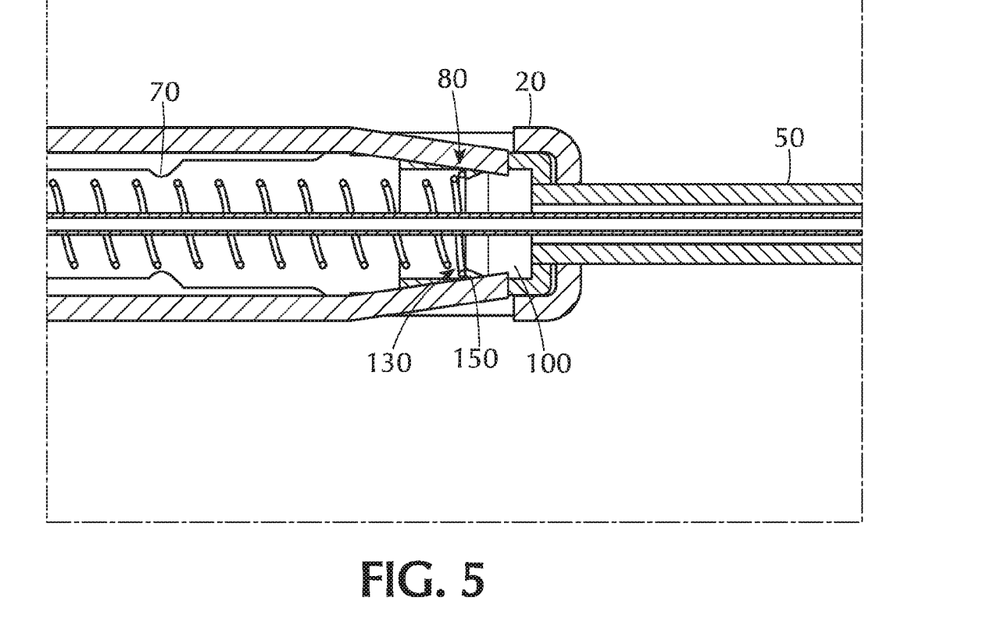
FIG. 5 is a plan view of the safety needle device prior to activation.
Figure 6:
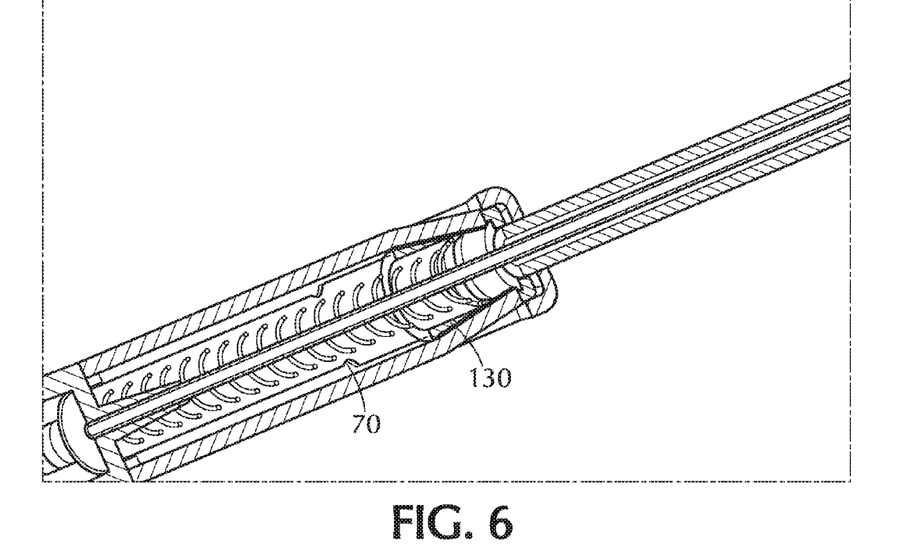
FIG. 6 is another plan view of the safety needle device prior to activation.

In one or more embodiments, as shown in FIG. 4, the spring 60 comprises a compression or coil spring having an enlarged end coil 130 on the distal end that has a diameter larger than the proximal end and main body of the spring 60 which is of a constant or smaller diameter, as shown in FIGS. 4 and 5. In one or more embodiments, as shown in FIGS. 5 and 6, the enlarged coil portion rests on the ledge 150 when the spring 60 is in the proximal spring position 80. In one or more embodiments, the enlarged coil portion rests on the catch 100 to lock the retractable sheath 50 when the spring is in the distal spring position 90, and the retractable sheath is in the distal position of the housing.

In one or more embodiments, the catch 100 is defined by inward ramps terminating in barbed ends.

In one or more embodiments, the retractable sheath 50 fully covers the needle 40 when the spring is in the distal position of the housing.

Figure 7:
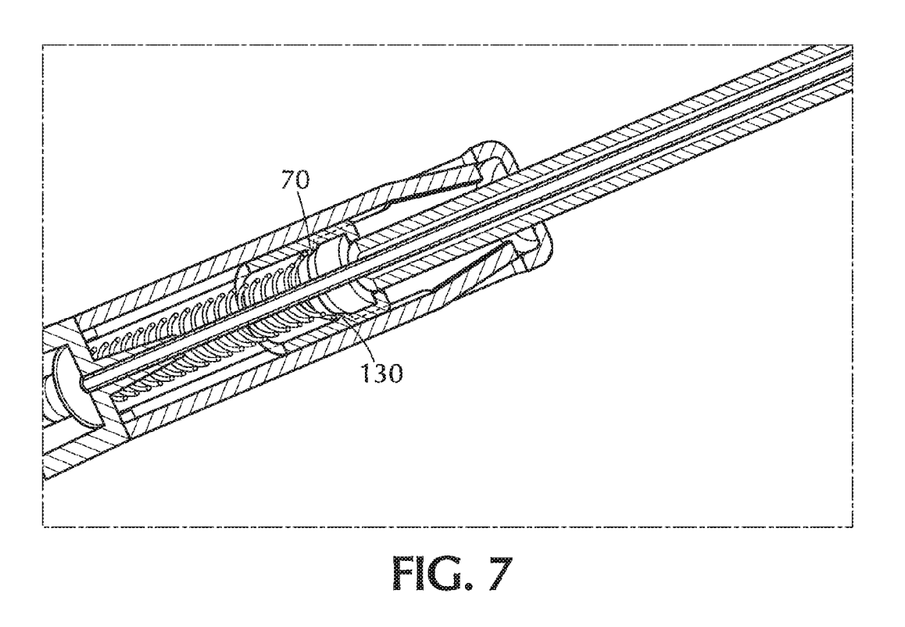
FIG. 7 is another plan view of the safety needle device prior to activation.
Figure 8:
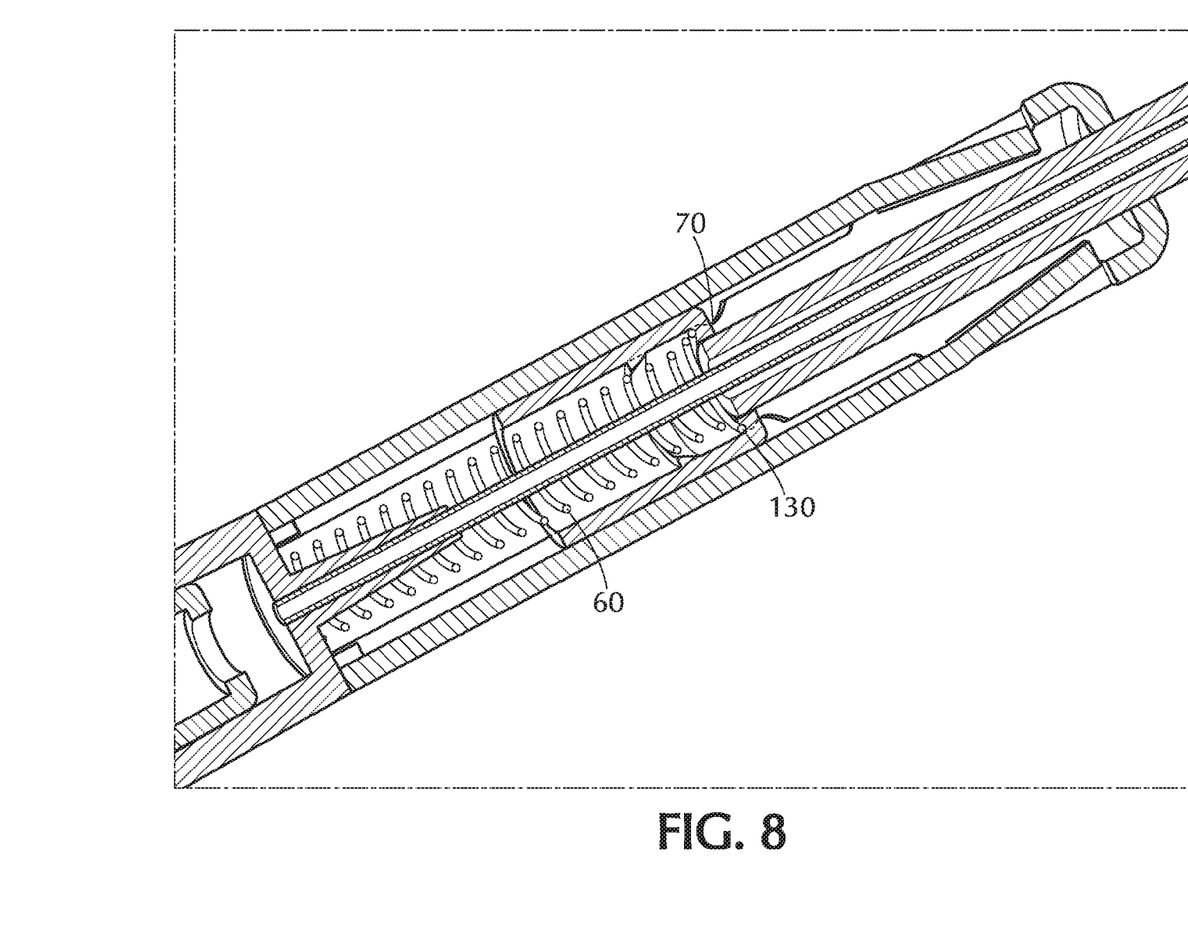
FIG. 8 is a plan view of the safety needle device after activation.

In one or more embodiments, the radial protrusion 70 is configured to provide free movement between the radial protrusion 70 and the proximal end and main body of the spring 60. In one or more embodiments, the radial protrusion 70 is configured to provide hindered movement between the radial protrusion 70 and the enlarged end coil 130. In one or more embodiments, as shown in FIGS. 7 and 8, the radial protrusion 70 compresses the enlarged end coil 130 to cause the enlarged end coil 130 to slip from the ledge 150 and move from the proximal spring position 80 to the distal spring position 90. In some embodiments, the radial protrusion 70 is located on the proximal end of the housing. In other embodiments, the radial protrusion 70 is located on the distal end of the housing.

Upon administration of the injection, the retractable sheath 50 moves from a distal to proximal position and the needle tip is exposed so that the needle tip may penetrate the injection site. Upon continued application of force by pressing sheath 50 against the skin at the location where it is desired to insert needle 40, sheath 50 retracts into housing 20 allowing the injection site to be penetrated by the needle tip. As shown in FIG. 3, the enlarged end coil 130 is retained on the ledge 150 and cannot lock on the catch, and therefore the retractable sheath 50 is not locked into place.

Figure 9:
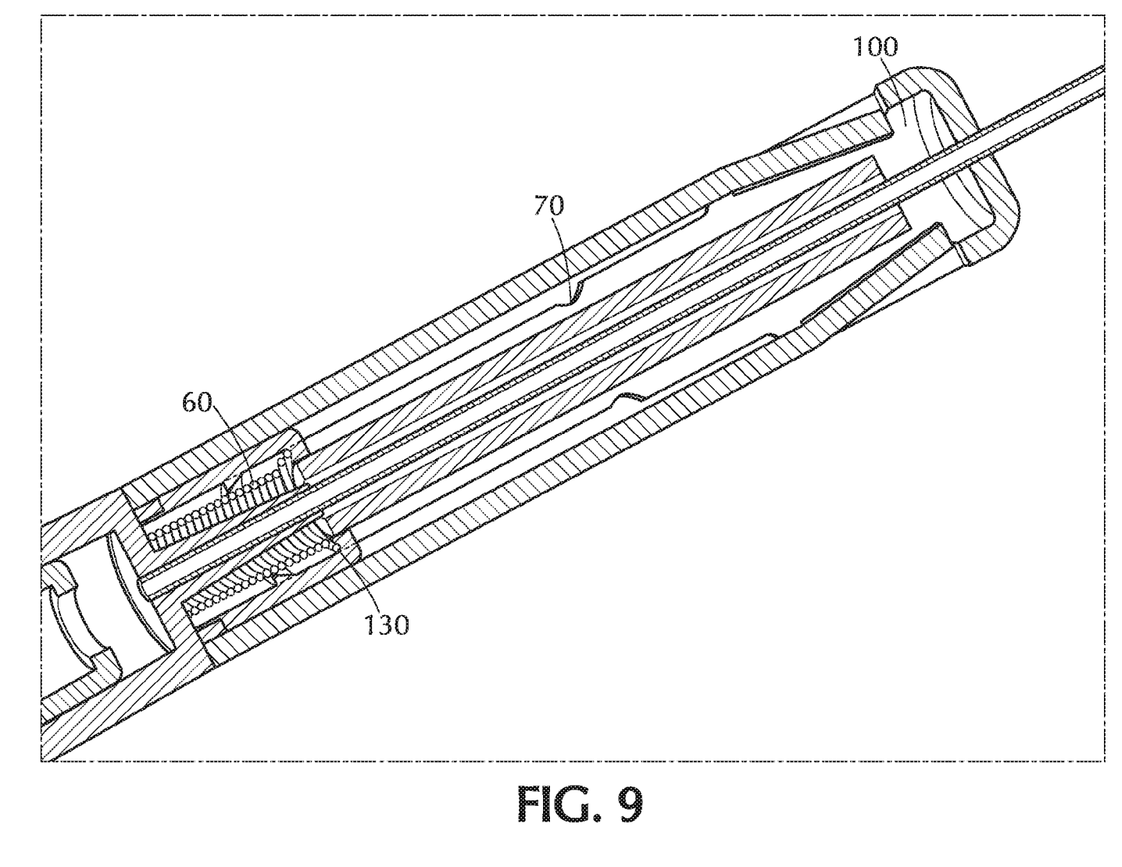
FIG. 9 is a plan view of the safety needle device after activation at the bottom of travel.
Figure 10:
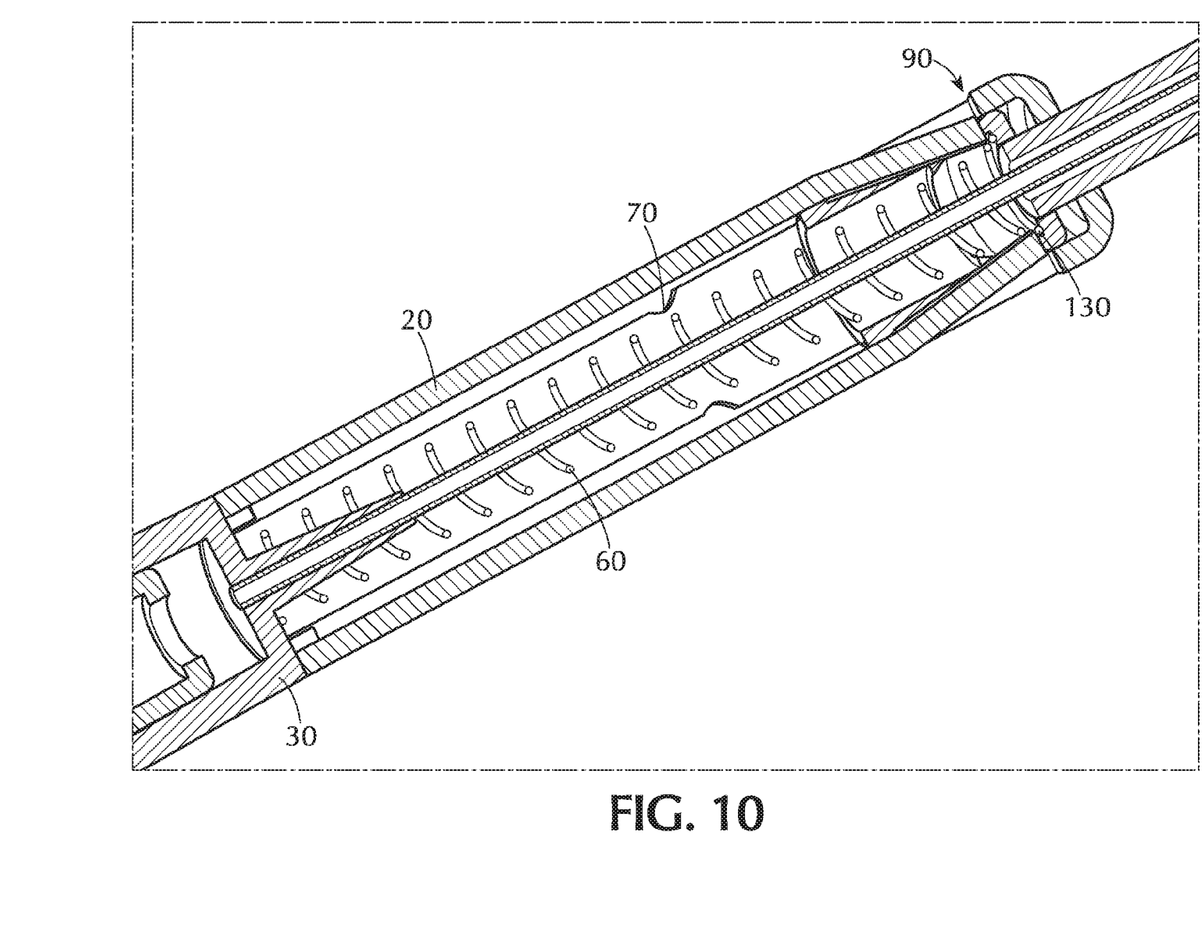
FIG. 10 is a plan view of the safety needle device after activation showing enlarged end coil section locked in catch.

As shown in FIG. 5, there is a clearance between the radial protrusion 70 and the main body of the spring 60. As shown in FIG. 7, the radial protrusion 70 is sized such that it will interfere with the enlarged end coil 130 as it passes over causing the enlarged end coil 130 to be compressed by the radial protrusion 70. As shown in FIG. 8, upon continued application of proximal force, the enlarged end coil 130 is compressed and becomes too small to be retained on the ledge 150, thereby slipping off the ledge 150. The radial protrusion 70 can be placed at any point in the housing 20 such that activation, whereby the retractable sheath 50 will lock if the safety needle device 10 is pulled out, can occur either at a very distal point in the housing, near the beginning of the stroke as soon as the coil clears the barbs in the housing, or at a proximal point in the housing, for example, the bottom of the stroke, as shown in FIG. 9, when the needle 40 is fully inserted into the injection site, or at any position along the length of the housing. As shown in FIG. 10, as the injection is completed and the needle 40 is pulled from injection site, the spring force causes the sheath 50 to extend, and at the end of the stroke, the enlarged end coil 130 advances past the catch 100 at the end of the stroke to lock the retractable sheath 50 thereby completing a passive safety lock-out.

Constant Diameter Spring with Radially Compressible Member

In another embodiment of the present invention, it is envisioned that the spring 60 has a constant diameter having a radially compressible member 160, for example C-clip, attached to or biased against its distal end wherein the radially compressible member 160 rests on a ledge 150.

Figure 11:
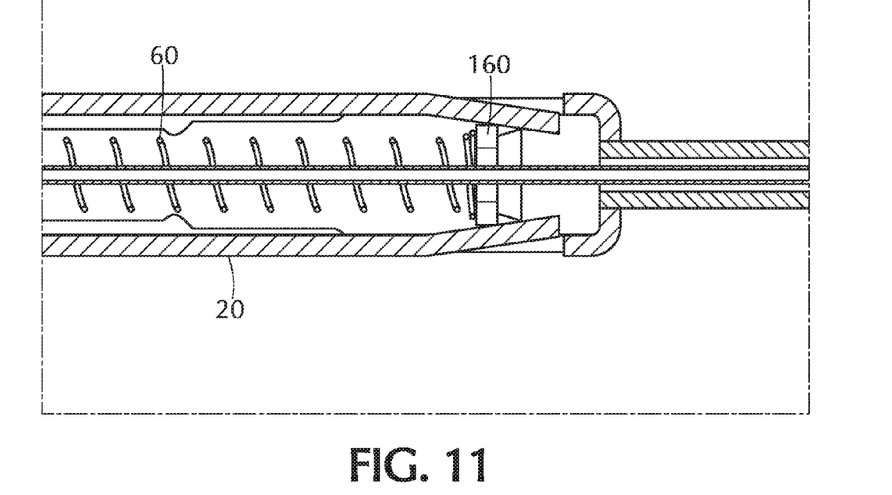
FIG. 11 is a plan view of the safety needle device in accordance with an alternative embodiment of the present invention.

As shown in FIG. 11, the present invention is also directed to a safety needle device including a housing 20 having a proximal end and a distal end having an opening; a needle 40 having a distal end and a proximal end mounted to a needle hub 30 at the proximal end of the housing; a retractable sheath 50 disposed an outer surface on the distal end of the housing 20 surrounding the needle 40, the retractable sheath 50 having a radially enlarged proximal end defining a proximal spring position 80 and a distal spring position 90 separated by a ledge 150; a spring 60 to bias the retractable sheath 50 in a distal direction to cover the distal end of the needle 40, the spring 60 having a distal end; and a radially compressible member on the distal end of the spring 60 having a larger diameter than the proximal end and main body of the spring 60; and a radial protrusion 70 extending inwardly from the housing 20 to cause the radially compressible member to compress upon an application of force or motion in the proximal direction to allow the radially compressible member to move from a proximal position to the distal position so that when the spring is extended, the radially compressible member is secured to a catch 100 at the distal end of the housing. In one or more embodiments, the proximal end of the housing may be connectable to a luer connection or other fluid connector, or integrated into a device, such as a syringe.

Upon administration of an injection, proximally directed force results in the radially compressible member progressing to the radial protrusion 70 extending outwardly from housing. After reaching the radial protrusion 70, continued proximally directed force results in the compression of the radially compressible member allowing the compressed radially compressible member to slip off the ledge 150 causing the compressible member to advance from a proximal to distal position in the housing. As the compressible member advances from a proximal to distal position in the housing, the radially compressible member advances past the catch 100 to lock the retractable sheath 50 completing a passive safety lock-out.

In one or more embodiments, the radially compressible member rests on the ledge 150 when the member is in the proximal position. In one or more embodiments, the radially compressible member rests on the catch 100 to lock the retractable sheath 50 when the member is in a distal position, and the retractable sheath is in the distal position of the housing.

Internal Configuration with Reduced End Coil Spring

In another embodiment of the present invention, it is envisioned that the internal locking components may be inverted so that the spring activates and locks on component features on the inside of the spring, rather than outside of its coils. In such an embodiment, a needle hub 30 extending to the tip of the housing 20 includes radial outward protrusion, locking barb, and ledge 150 that interact with a shrunken end coil on the inside of the spring.

Figure 12:
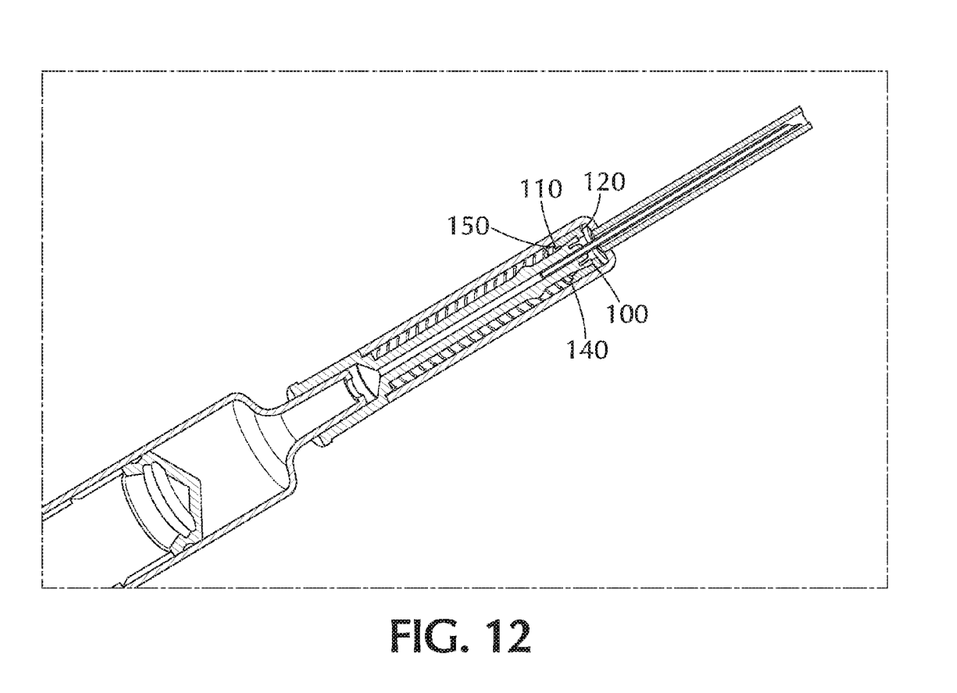
FIG. 12 is a plan view of the safety needle device in accordance with yet another alternative embodiment of the present invention.

As shown in FIG. 12, the present invention is also directed to a safety needle device 10 including a housing 20 having a proximal end and a distal end having an opening; a needle 40 having a distal end and a proximal end mounted to a needle hub 30 at the proximal end of the housing; a needle hub 30 having a radial protrusion 70 extending outward into housing 20 and a distal end having a ramped surface; a retractable sheath 50 having a proximal end and distal end, the proximal end having a first flange 110 forming a ledge 150 with the ramped surface of the needle hub 30 and a second flange 120 to hold the retractable sheath 50 in the housing, the retractable sheath 50 surrounding a needle 40 having a distal end and a proximal end mounted to the needle hub 30 at the proximal end of the housing, the first and second flange 120 defining a proximal spring position 80 and a distal spring position 90; a spring to bias the retractable sheath 50 in a distal direction to cover the distal end of the needle 40, the spring having a proximal end, a main body, and a distal end; the radial protrusion causing the spring to move from the proximal spring position 80 to the distal spring position 90 when the spring is extended; and a catch 100 forming at the distal end of the ramped surface between the ramped surface and the second flange 120 of the retractable sheath 50.

In one or more embodiments, the spring comprises a reduced end coil 140 on the distal end having a smaller diameter than the proximal end and main body of the spring. In one or more embodiments, the reduced end coil 140 rests on the ledge 150 when the spring is in the proximal spring position 80. In one or more embodiments, the reduced end coil 140 rests on the catch 100 to lock the retractable sheath 50 when the spring is in the distal spring position 90.

In one or more embodiments, the catch 100 is defined by a recess formed between the outward ramped surface of the needle hub 30 and the second flange 120 of the retractable sheath 50.

In one or more embodiments, the radial protrusion 70 is configured to provide free movement between the radial protrusion 70 and the proximal end and main body of the spring. In one or more embodiments, the radial protrusion 70 is configured to provide hindered movement between the radial protrusion 70 and the reduced end coil 140. In one or more embodiments, the radial protrusion 70 enlarges the reduced end coil 140 to cause the reduced end coil 140 to slip from the ledge 150 and move from the proximal spring position 80 to the distal spring position 90. In one or more embodiments, the radial protrusion 70 is located proximally to the ledge 150.

In one or more embodiments, the proximal end of the housing may be connectable to a luer connection or other fluid connector, or integrated into a device, such as a syringe.

Upon administration of the injection, the retractable sheath 50 moves from a distal to proximal position and the needle tip is exposed so that the needle tip may penetrate the injection site. Upon continued application of force by pressing sheath 50 against the skin of a patient at the location where it is desired to insert needle 40, sheath 50 retracts into housing 20 allowing the injection site to be penetrated by the needle. As shown in FIG. 12, the reduced end coil 140 is retained on the ledge 150 and cannot lock on the catch, and therefore the retractable sheath 50 is not locked into place.

As shown in FIG. 12, there is a clearance between the radial protrusion 70 and the main body of the spring. As shown in FIG. 12, the radial protrusion 70 is sized such that it will interfere with the reduced end coil 140 as it passes over causing the reduced end coil 140 to be expand. As shown in FIG. 12, upon continued application of proximal force, the reduce end coil is expanded and becomes too large to be retained on the ledge 150, thereby slipping off the ledge 150. The radial protrusion 70 can be placed at any point in the housing 20 such that activation, whereby the retractable sheath 50 will lock if the safety needle device 10 is pulled out, can occur either at a very distal point in the housing, near the beginning of the stroke as soon as the coil clears the barbs in the housing, or at a proximal point in the housing, for example, the bottom of the stroke when the needle 40 is fully inserted into the injection site, or at any position along the length of the housing. Upon continued application of proximal force as the injection is completed, reduced end coil 140 extends past the ramped surface and advances into the catch 100 at the end of the stroke to lock the retractable sheath 50 thereby completing a passive safety lock-out.

In yet another embodiment, an orientation similar to the one described herein for internal configuration with reduced end coil spring is also envisioned using the constant diameter spring with radially compressible member.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A safety needle device comprising:
   a housing having a proximal end and a distal end having an opening;
   a retractable sheath disposed and movable in the opening and surrounding a needle cannula having a distal end and a proximal end mounted to a needle hub at the proximal end of the housing, the retractable sheath having a radially enlarged proximal end defining a proximal spring position and a distal spring position separated by a ledge;
   a spring to bias the retractable sheath in a distal direction to cover the distal end of the needle cannula, the spring having a proximal end, a main body, and a distal end, the spring comprises an enlarged coil portion on the distal end having a larger diameter than the proximal end and main body of the spring;
   a radial protrusion extending inward into housing to cause the spring to move from the proximal spring position to the distal spring position so that when the spring is extended, the distal end of the spring is secured to a catch at the distal end of the housing, wherein the radial protrusion compresses the enlarged coil portion to cause the enlarged coil portion to slip from the ledge and move from the proximal spring position to the distal spring position.

2. The safety needle device of claim 1, wherein the enlarged coil portion rests on the ledge when the spring is in the proximal spring position.

3. The safety needle device of claim 1, wherein the enlarged coil portion rests on the catch to lock the retractable sheath when the spring is in the distal spring position.

4. The safety needle device of claim 1, wherein the catch is defined by inward ramps terminating in barbed ends.

5. The safety needle device of claim 1, wherein the radial protrusion is configured to provide free movement between the radial protrusion and the proximal end and main body of the spring.

* * * * *